United States Patent [19]

Rippel et al.

[11] Patent Number: 5,166,346
[45] Date of Patent: Nov. 24, 1992

[54] PROCESS FOR THE PREPARATION OF THIOPHENE DERIVATIVES AND ALSO NEW DIHYDROTHIOPHENE 1-OXIDES

[75] Inventors: Robert Rippel, Hofheim am Taunus; Hans-Wolfram Flemming, Usingen; Manfred Rukwied, Kelkheim, all of Fed. Rep. of Germany

[73] Assignee: Hoechst Akteingesellschaft, Frankfurt am Main, Fed. Rep. of Germany

[21] Appl. No.: 630,434

[22] Filed: Dec. 20, 1990

Related U.S. Application Data

[63] Continuation of Ser. No. 449,443, Dec. 11, 1989, abandoned, which is a continuation of Ser. No. 310,189, Feb. 14, 1989, abandoned.

[30] Foreign Application Priority Data

Feb. 16, 1988 [DE] Fed. Rep. of Germany ....... 3804794

[51] Int. Cl.$^5$ .................. C07D 413/00; C07D 405/00; C07D 333/38; C07D 333/36
[52] U.S. Cl. .................................... 544/146; 544/379; 546/212; 546/213; 548/527; 549/61; 549/68; 549/69
[58] Field of Search .............................. 549/61, 68, 69; 548/527; 546/212, 213; 544/146, 379

[56] References Cited

U.S. PATENT DOCUMENTS

| | | | |
|---|---|---|---|
| 2,443,598 | 6/1948 | Cheney et al. | 549/68 |
| 3,445,473 | 5/1969 | Ruschig et al. | 549/68 |
| 3,855,243 | 12/1974 | Ruschig . | |
| 4,239,897 | 12/1980 | Rossy et al. . | |
| 4,242,518 | 12/1980 | Rossy et al. . | |

FOREIGN PATENT DOCUMENTS 1643325 12/1976 Fed. Rep. of Germany .
WO87/02220 4/1987 PCT Int'l Appl. .
2194530 3/1988 United Kingdom .

OTHER PUBLICATIONS

Fieser et al., Reagents for Organic Synthesis, vol. 4, p. 8.
W. Theilheimer, Synthetic Methods of Organic Chemistry, vol. 17, p. 233, 1963.
A. P. Stoll & R. Suess, Helvetica Chimica Acta, vol. 57, Fasc. 8 (1974) Nos. 269-270, pp. 2487-2492.
T. Takaya et al., Bull. Chem. Soc. Japan, vol. 41 (1968), pp. 2086-2095.

*Primary Examiner*—Alan Siegel
*Attorney, Agent, or Firm*—Finnegan, Henderson, Farabow, Garrett and Dunner

[57] ABSTRACT

Process for the preparation of thiophene derivatives and also new dihydrothiophene 1-oxides.

Thiophene derivatives having an—optionally substituted—amino group on the thiophene ring are prepared by dehydrogenating dihydrothiophenes, substituted in a manner identical to that of the desired thiophene derivatives, by means of $H_2O_2$, the dihydrothiophenes being reacted with $H_2O_2$ in a first reaction stage in a neutral medium to give the corresponding sulfoxides, which are then rearranged into the thiophene derivatives by means of acid in the second reaction stage.

The dihydrothiophene 1-oxides formed as intermediates in this reaction are new compounds. Like the thiophene derivatives formed from them by rearrangement with acid, they are intermediates, mainly in the sector of plant protection agents and pharmaceuticals.

14 Claims, No Drawings

PROCESS FOR THE PREPARATION OF THIOPHENE DERIVATIVES AND ALSO NEW DIHYDROTHIOPHENE 1-OXIDES

This application is a continuation of application Ser. No. 07/449,443, filed Dec. 11, 1989, now abandoned, which is a continuation of application Ser. No. 07/310,189, filed Feb. 14, 1989, now abandoned.

It is known that thiophene derivatives can be prepared by dehydrogenating dihydrothiophenes, examples of the dehydrogenating agents used being chlorides and bromides of sulfuric or phosphoric acid, chlorine, bromine, N-halogen compounds, tetrachloroquinone (chloranil), nitrosobenzene, iodosobenzene, selenium or sulfur. Hydrogen peroxide $H_2O_2$ has also already been described as a dehydrogenating agent for specific cases; cf., for example, A. P. Stoll and R. Süess, Helvetica Chimica Acta volume 57, Fasc. 8 (1974) No. 269-270, pp. 2487-2492. In this literature reference 4-ethoxycarbonyl-3-hydroxy-2-phenyldihydrothiophene is dehydrogenated with $H_2O_2$ in ethanolic solution at 60°-65° C. to give the corresponding thiophene derivative; the reaction takes place in accordance with the following equation:

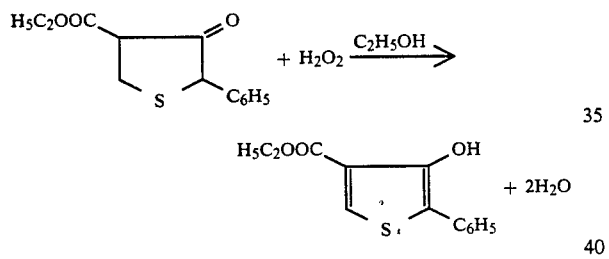

The yield for this reaction is quoted as 90%.

Other dihydrothiophenes—namely those carrying, as substituents, electron-donating groups, such as, for example, the amino group or a substituted amino group—do not afford the corresponding thiophene derivatives with $H_2O_2$ in glacial acetic acid, but instead the dihydrothiophene sulfones; cf. T. Takaya et al., Bull. Chem. Soc. Japan, volume 41, pp. 2086-2095 (1968). An example particularly described in this literature reference is the reaction of 3-ethoxycarbonylamino-4-ethoxycarbonyl-2,5-dihydrothiophene with $H_2O_2$/glacial acetic acid:

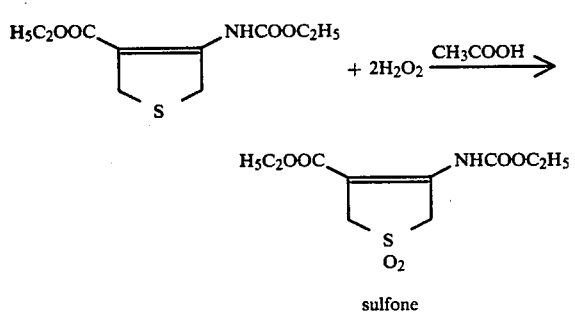

sulfone

It has now been found that it is also possible to dehydrogenate those dihydrothiophenes which carry the amino group or a substituted amino group as substituents by means of $H_2O_2$ to give the corresponding thiophene derivatives, if the dehydrogenation is carried out in two stages, namely first reacting the dihydrothiophenes with $H_2O_2$ in a neutral medium, in the course of which the dihydrothiophene 1(=S)oxides are formed, and then adding an acid to the dihydrothiophene 1-oxides—with or without isolation of the latter—in the course of which the rearrangement to give the corresponding thiophene derivatives takes place.

The invention therefore relates to a process for the preparation of thiophene derivatives of the formula I

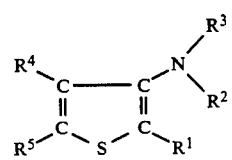

which $R^1$-$R^5$ independently of one another denote hydrogen (H) or organic radicals by dehydrogenating dihydrothiophenes of the formulae IIa and/or IIb

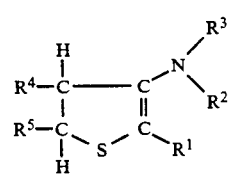

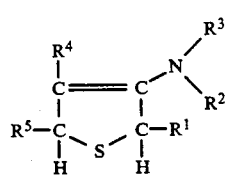

in which the radicals $R^1$-$R^5$ have the same meaning as in formula I, which comprises carrying out the dehydrogenation by means of $H_2O_2$ and in 2 stages, a) by reacting the dihydrothiophenes of the formulae IIa and/or IIb with an at least approximately equimolar amount of $H_2O_2$ in a neutral solvent or diluent in the absence of acid(s), in the course of which the 1-oxides of the initial dihydrothiophenes are formed, and b) by adding an acid to the dihydrothiophene 1-oxides formed in stage a), with or without the isolation of the latter, in the course of which the dihydrothiophene 1-oxides undergo rearrangement to give the thiophene derivatives of the formula I.

In terms of formulae the process can be represented as follows:

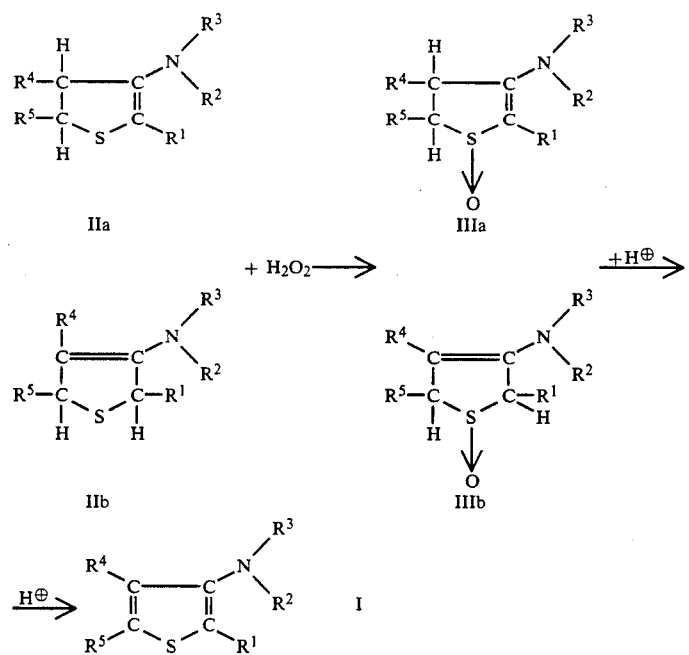

The invention also relates to the two individual process stages a) and b) and to the dihydrothiophene 1-oxides (of the formulae IIIa/IIIb) formed in stage a).

It could not have been expected and is, therefore, extremely surprising that the reaction of T. Takaya et al. (loc. cit.) starting from dihydrothiophenes substituted by amino groups and from $H_2O_2$ can be guided by the modification according to the invention into a completely different direction—namely to the formation of the corresponding thiophene derivatives (instead of the dihydrothiophene sulfones). The decisive factor for this different course is quite evidently that no acid is present at the start of the reaction.

The process affords high yields and purities of the products and is extremely non-harmful in terms of the environment and waste disposal. Hitherto it has only been possible to convert dihydrothiophenes substituted by amino groups into the corresponding thiophene derivatives using dehydrogenating agents which are less harmless in terms of the environment and waste disposal; the ability also to carry out this conversion by means of $H_2O_2$—from which no byproducts other than water are formed—constitutes an outstanding advantage and advance.

The substituents $R^1$ to $R^5$ in the abovementioned formulae I, IIa/IIb and IIIa/IIIb can—independently of one another—be H or organic radicals.

Organic radicals preferred for $R^1$, $R^4$ and $R^5$ are optionally substituted aliphatic radicals, cycloaliphatic and araliphatic radicals, optionally substituted aromatic radicals, alkoxycarbonyl, carboxamido, acyl radicals or CN; preferred organic radicals for $R^2$ and $R^3$ are optionally substituted aliphatic radicals, cycloaliphatic and araliphatic radicals, optionally substituted aromatic radicals and acyl radicals; in addition one of the two radicals $R^2$ or $R^3$ can also denote alkoxycarbonyl, or $R^2$ and $R^3$, together with the N atom to which they are attached, can also form a 5-membered to 7-membered ring which can also contain another heteroatom of the type O, S or N as a ring member and can also be substituted.

The following organic radicals are particularly preferred for $R^1$ to $R^5$:

$R^1$, $R^4$ and $R^5$: $C_1$–$C_4$-alkyl, $C_5$–$C_6$-cycloalkyl, $CH_2$–$C_6H_5$, $C_6H_5$, $COOCH_3$, $COOC_2H_5$, $CONH_2$, $COCH_3$, $COC_2H_5$ or CN;

$R^2$ and $R^3$: $C_1$–$C_4$-alkyl, optionally substituted by $COOCH_3$ or $COOC_2H_5$, $C_5$–$C_6$-cycloalkyl, $(CH_2)_{1-3}$–$C_6H_5$, $C_6H_5$, optionally substituted by OH, $OCH_3$, $OC_2H_5$, F, Cl or Br, or $CO(C_1$–$C_5$-alkyl) in which the alkyl radical can be substituted by OH, F, Cl, Br, $(C_1$–$C_4)$-alkoxy, $NH_2$ or $(C_1$–$C_8)$-alkylamino groups, and one of the radicals $R^2$ or $R^3$ can, in addition, also be $COOCH_3$ or $COOC_2H_5$, or $R^2$ and $R^3$, together with the N atom to which they are attached, can form a pyrrolidino, piperidino, morpholino, piperazino or homopiperazino ring.

The starting dihydrothiophenes of the formulae IIa and IIb are either known from the literature or can be prepared analogously to known processes. Known processes are, for example, quoted in the abovementioned literature reference of T. Takaya et al. (loc. cit.)—cf. especially page 2090—and in DE-C 1,643,325. A summarizing recent survey is contained in the book by Weissberger, The Chemistry of Heterocyclic Compounds, A Series of Monographs, Arnold Weissberger and Edward C. Taylor, volume 44/part 21 "Thiophene and Its Derivatives", edited by S. Gronowitz (1986).

The starting dihydrothiophenes are reacted in stage a) of the process according to the invention with an at least approximately equimolar amount—preferably with an approximately 1-molar to 2-molar amount—of $H_2O_2$ in a neutral solvent or diluent and in the absence of acid(s).

Suitable neutral solvents or diluents are water and/or neutral organic solvents. The following may be mentioned as examples of neutral organic solvents:

alcohols, such as, for example, methanol, ethanol, 1-propanol, isopropanol, 1-butanol, 2-butanol, tert.-butanol or 2-methylpropanol;

aliphatic and cycloaliphatic hydrocarbons, such as, for example, pentane, 2-methylbutane, hexane, 2,2-dimethylbutane, 2,3-dimethylbutane, 2-methylpentane, 3-methylpentane, heptane, cyclohexane, methylcyclohexane, 1,2-dimethylcyclohexane, 1,3-dimethylcyclohexane or 1,4-dimethylcyclohexane;

aromatic hydrocarbons, such as, for example, toluene, xylenes or isopropylbenzene;

aliphatic and aromatic halogenated hydrocarbons, such as, for example, tetrachloroethylene, 1,1,2,2-tetrachloroethane, 1,1,1,2-tetrachloroethane, methylenechloride, dichloropropane, carbon tetrachloride, 1,1,2-trichloro-1,2,2-trifluoroethane, trichlorofluoromethane, 1,2-dichloroethane, 1,1-dichloroethane or chlorobenzene;

ethers, such as, for example, diethyl ether, di-n-butyl ether, diisopropyl ether, diisoamyl ether, methyl tert.-butyl ether, ethylene glycol dimethyl ether, tetrahydrofuran, dioxane or anisole;

esters, such as, for example, methyl acetate, ethyl acetate or butyl acetate;

acid amides, such as, for example, dimethylformamide or dimethylacetamide.

Solvents or diluents which are particularly preferred are water and $C_1$–$C_4$-alkanols (in particular ethanol and isopropanol), on their own or mixed with one another.

The reaction temperature in stage a) can vary within a fairly wide range. In general, the reaction temperature here is between about $-20°$ and about $+100°$ C., preferably between about $-15°$ and about $+70°$ C.

In order to carry out the reaction, the appropriate dihydrothiophenes of the formulae IIa and/or IIb are first dissolved or suspended in an appropriate neutral solvent or diluent. The corresponding amount of $H_2O_2$—preferably also mixed with one or more of the solvents or diluents mentioned above—is then added dropwise in a normal manner and the mixture is kept at the reaction temperature until starting material can no longer be detected; the detection is carried out in a customary manner, preferably by taking a sample and carrying out a thin layer chromatogram.

The dihydrothiophene 1-oxides of the formulae IIIa or IIIb formed can be isolated either by cooling and filtering off with suction or by concentrating the solution. They can in some cases be formed as mixtures of diastereomers, and these can be separated by chromatography. The dihydrothiophene 1-oxides of the formulae IIIa and IIIb are new compounds.

In the course of the rearrangement according to stage b) of the process according to the invention the dihydrothiophene 1-oxides of the formulae IIIa and IIIb afford the equivalent thiophene derivatives. For this rearrangement it is possible to redissolve or resuspend the dihydrothiophene 1-oxides which have been isolated in one of the abovementioned solvents or diluents, or the reaction mixture obtained in stage a) can be processed further directly as such.

An acid is added dropwise or introduced in the form of gas (HCl or HBr) into the solution or suspension. Depending on the starting compounds, catalytic or larger amounts of acid are preferable or necessary for this.

The acids used can be inorganic and/or organic acids. Aqueous, alcoholic or ethereal solutions of hydrogen chloride or hydrogen bromide or sulfuric acid are preferred.

The reaction temperature possible embraces the range between the solidification point and the boiling point of the solvent or diluent used; room temperature is preferred for this reaction.

The mixture is worked up in a customary manner. The free aminothiophenes can be obtained in a known manner from the aminothiophene salts formed in a given case.

The new dihydrothiophene 1-oxides and also the known thiophene derivatives formed by the rearrangement thereof in accordance with the process of the invention are valuable starting materials or intermediates for the preparation of, in particular, plant protection agents and pharmaceuticals. Examples of pharmaceuticals which may be mentioned here are the substituted 3-aminoacylaminothiophenes of the general formula IV below, which are described in DE-C 1,643,325 mentioned above and which are suitable, above all, as local anesthetics:

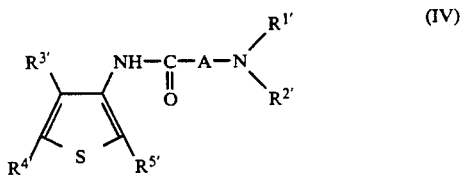

in which $R^{1'}$ is H or an organic radical, $R^{2'}$ is an organic radical or $R^{1'}$ and $R^{2'}$ can also—together with the N atom to which they are attached—form a ring, $R^{3'}$–$R^{5'}$ or organic radicals and A is a $C_1$–$C_4$-alkylene group.

The compounds are prepared, for example, in accordance with variant b)) of the process of the DE-C text, as follows:

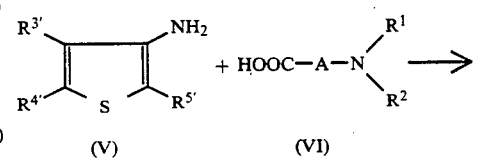

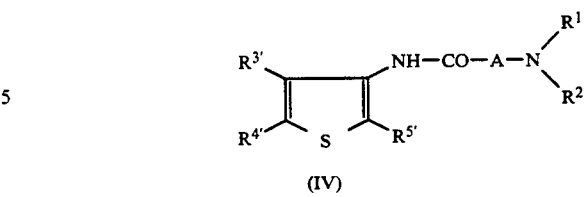

The starting materials (V) can be prepared more advantageously and in a manner less harmful to the environment than hitherto by the process according to the invention via the new intermediates IIIa/IIIb.

The following examples serve to illustrate the invention without, however, limiting the latter. The melting points and decomposition points quoted are not corrected and depend on mixtures of diastereomers which may be formed.

EXAMPLE 1 a) 3-Amino-4-methoxycarbonyl-2,5-dihydrothiophene 1-oxide 3.2 g (0.02 mol) of 3-amino-4-methoxycarbonyl-2,5-dihydrothiophene are suspended in 30 ml of isopropanol. 2.2 ml of 35% strength hydrogen peroxide are added, with cooling. The mixture is then stirred at an internal temperature of 50° C. until starting material can no longer be detected in a thin layer chromatogram (approx. 5 hours). The mixture is then cooled in an ice bath and the precipitated crystals are filtered off with suction and washed with ice-cold isopropanol and with diethyl ether. Yield: 3.5 g (91% of theory). When recrystallized from methanol, the crystals melt at 137°–140° C.

A number of other dihydrothiophene 1-oxides were prepared analogously; the details can be seen from Table 1.

isopropanol. 5 ml of a 5N solution of hydrogen chloride in isopropanol are added dropwise, with ice cooling, and the mixture is then stirred for approx. 1 hour at a bath temperature of 60° C. When the thin layer chromatogram indicates complete reaction, the suspension is evaporated to dryness on a rotary evaporator, and the residue is triturated with a little ethyl acetate and the product is filtered off with suction and dried. Yield: 2.8 g (89% of theory); melting point 194°–201° C.).

The thiophene derivatives in Table 2 were prepared analogously.

TABLE 1

| No. | $R^1$ | $R^2$ | $R^3$ | $R^4$ | $R^5$ | m.p. (°C.) |
|---|---|---|---|---|---|---|
| 1a | H | H | H | COOCH$_3$ | H | 137–140 |
| 1b | COOCH$_3$ | H | H | CH$_3$ | H | 212–218 |
| 1c | H | H | H | CN | H | 165–167 |
| 1d | H | —(CH$_2$)$_2$C$_6$H$_5$ | H | COOCH$_3$ | H | oil |
| 1e | COOCH$_3$ | —COCH$_3$ | H | CH$_3$ | H | 93–98 |
| 1f | H | —COCH$_3$ | H | —COOCH$_3$ | H | 119–122 |
| 1g | H | —COOC$_2$H$_5$ | H | —COOCH$_3$ | H | oil |
| 1h | COOCH$_3$ | —COOC$_2$H$_5$ | H | CH$_3$ | H | 132–135 |
| 1i | COOCH$_3$ | —C$_6$H$_4$-4-OCH$_3$ | H | CH$_3$ | H | 158–165 |
| 1k | COOCH$_3$ | —CH$_3$ | H | CH$_3$ | H | oil |
| 1l | H | CH$_3$ | C$_6$H$_5$ | CN | H | oil |
| 1m | H | CH$_3$ | CH$_3$ | CN | H | 88–93 |
| 1n | CH$_3$ | H | H | COOCH$_3$ | H | 131–138 |
| 1o | COCH$_3$ | H | H | CH$_3$ | H | 171–175 |
| 1p | H | COCH$_3$ | H | CN | H | oil |
| 1q | COOCH$_3$ | CH$_2$—COOC$_2$H$_5$ | H | CH$_3$ | H | 93–98 |
| 1r | COOCH$_3$ | CH$_2$—COOCH$_3$ | H | CH$_3$ | H | oil |
| 1s | COOCH$_3$ | CH$_3$<br>\|<br>OC—CH—NHC$_3$H$_7$ | H | CH$_3$ | H | oil |

EXAMPLE 2

3-Amino-4-methoxycarbonylthiophene 3.8 g (0.02 mol) of 3-amino-4-methoxycarbonyl-2,5-dihydrothiophene 1-oxide are suspended in 20 ml of

TABLE 2

| No. | $R^1$ | $R^2$ | $R^3$ | $R^4$ | $R^5$ | m.p. (°C.) |
|---|---|---|---|---|---|---|
| 2a | H | H | H | COOCH$_3$ | H | 194–201 (HCl) |
| 2b | COOCH$_3$ | H | H | CH$_3$ | H | 128–131 (HCl) |
| 2c | H | H | H | CN | H | 214–216 (HCl) |
| 2d | H | —(CH$_2$)$_3$C$_6$H$_5$ | H | COOCH$_3$ | H | 145–148 (HCl) |
| 2e | COOCH$_3$ | COCH$_3$ | H | CH$_3$ | H | 117 |
| 2f | H | COCH$_3$ | H | COOCH$_3$ | H | 58–60 |
| 2g | H | —COOC$_2$H$_5$ | H | COOCH$_3$ | H | 49–52 |
| 2h | COOCH$_3$ | —COOC$_2$H$_5$ | H | CH$_3$ | H | 80–83 |
| 2i | COOCH$_3$ | —C$_6$H$_4$-4-OCH$_3$ | H | CH$_3$ | H | 97–100 |
| 2k | COOCH$_3$ | CH$_3$ | H | CH$_3$ | H | 151–154 (HCl) |
| 2l | H | C$_6$H$_5$ | CH$_3$ | CN | H | 52–53 |

TABLE 2-continued

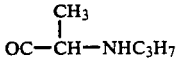

| No. | R¹ | R² | R³ | R⁴ | R⁵ | m.p. (°C.) |
|---|---|---|---|---|---|---|
| 2m | H | $CH_3$ | $CH_3$ | CN | H | 142–144 (HCl) |
| 2n | $CH_3$ | H | H | $COOCH_3$ | H | 154–159 (HCl) |
| 2o | $COCH_3$ | H | H | $CH_3$ | H | 161–162 (HCl) |
| 2p | H | $-COCH_3$ | H | CN | H | 162–167 |
| 2q | $COOCH_3$ | $-CH_2COOC_2H_5$ | H | $CH_3$ | H | 48–50 |
| 2r | $COOCH_3$ | $-CH_2-COOCH_3$ | H | $CH_3$ | H | 72–74 |
| 2s | $COOCH_3$ | $\underset{OC-CH-NHC_3H_7}{CH_3}$ | H | $CH_3$ | H | 175–176 (HCl) |

EXAMPLE 3

3-Amino-2-methoxycarbonyl-4-methylthiophene 3.46 g (0.02 mol) of 3-amino-2-carbomethoxy-4-methyl-4,5-dihydrothiophene are dissolved in 25 ml of isopropanol, and 2.2 ml of 35% strength hydrogen peroxide are added dropwise, with ice cooling. Stirring is continued for 30 minutes at room temperature. The mixture is then cooled with ice water and 4 ml of 5N hydrochloric acid in isopropanol are added. The mixture is then heated to 60° C. and is stirred at this temperature for approx. 90 minutes. It is worked up by distilling off the isopropanol, stirring the crystalline residue thoroughly in a little ethyl acetate and filtering off the product with suction and drying it.

Yield of hydrochloride: 3.86 g (=93% of theory), melting point 128°–130° C.

Melting point of free base: 85° C.

The compounds described in Example 2 can also be prepared analogously in a one-pot process.

We claim:

1. A process for the preparation of a thiophene derivative of the formula I:

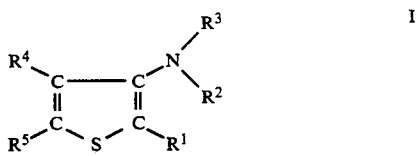

in which R¹ to R⁵, independently of one another, have the following meanings:

R¹, R⁴ and R⁵ are, independently of one another, hydrogen, $C_1-C_4$-alkyl radicals, $C_5-C_6$-cycloalkyl radicals, araliphatic radicals, aromatic radicals, alkoxycarbonyl, carboxamido, acyl radicals or CN; and R² and R³ are, independently of one another, hydrogen; $C_1-C_4$-alkyl radicals, optionally substituted by $COOCH_3$, $COOC_2H_5$, OH, F, Cl, Br, $(C_1-C_4)$-alkoxy, $NH_2$ or $(C_1-C_8)$-alkylamino groups; $C_5-C_6$-cycloalkyl radicals, araliphatic radicals or aromatic radicals, optionally substituted by OH, $OCH_3$, $OC_2H_5$, F, Cl or Br; or acyl radicals; and, in addition, one of the two radicals R² and R³ can also denote alkoxycarbonyl, or R² and R³, together with the N atom to which they are attached, can also form a 5-membered to 7-membered ring which can also contain another heteroatom of the type O, S or N as a ring member;

by dehydrogenating a dihydrothiophene having the formula IIa and/or IIb:

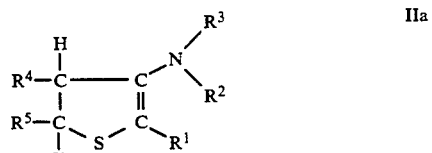

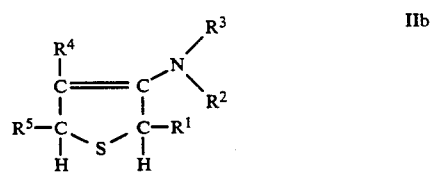

in which the radicals R¹ to R⁵ have the same meaning as in formula I, which comprises carrying out the dehydrogenation by means of $H_2O_2$ and in two stages, (a) by reacting a dihydrothiophene of the formula IIa and/or IIb with an at least approximately equimolar amount of $H_2O_2$ in a neutral solvent or diluent in the absence of acid, in the course of which the 1-oxide of the initial dihydrothiophene is formed, and (b) by adding an acid to the dihydrothiophene 1-oxide formed in stage (a), with or without isolation of the latter, in the course of which the dihydrothiophene 1-oxide undergoes rearrangement into the thiophene derivative of the formula I.

2. A process for the preparation of a dihydrothiophene 1-oxide of the formula IIIa or IIIb:

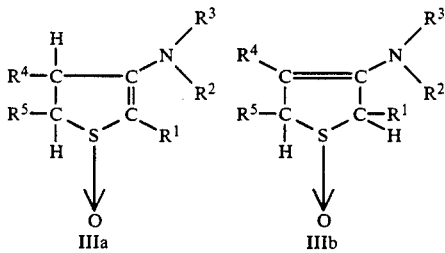

IIIa    IIIb in which $R^1$ to $R^5$, independently of one another, have the following meanings:

$R^1$, $R^4$ and $R^5$ are, independently of one another, hydrogen, $C_1$–$C_4$-alkyl radicals, $C_5$–$C_6$-cycloalkyl radicals, araliphatic radicals, aromatic radicals, alkoxycarbonyl, carboxamido, acyl radicals or CN; and $R^2$ and $R^3$ are, independently of one another, hydrogen; $C_1$–$C_4$-alkyl radicals, optionally substituted by $COOCH_3$, $COOC_2H_5$, OH, F, Cl, Br, ($C_1$–$C_4$)-alkoxy, $NH_2$ or ($C_1$–$C_8$)-alkylamino groups; $C_5$–$C_6$-cycloalkyl radicals, araliphatic radicals or aromatic radicals, optionally substituted by OH, $OCH_3$, $OC_2H_5$, F, Cl or Br; or acyl radicals; and, in addition, one of the two radicals $R^2$ and $R^3$ can also denote alkoxycarbonyl, or $R^2$ and $R^3$, together with the N atom to which they are attached, can also form a 5-membered to 7-membered ring which can also contain another heteroatom of the type O, S or N as a ring member;

which comprises reacting a dihydrothiophene of the formula IIa and/or IIb:

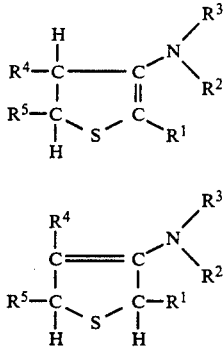

IIa

IIb in which $R^1$ to $R^5$ have the same meanings as in the formula IIIa and IIIb, with an at least equimolar amount of $H_2O_2$ in a neutral solvent or diluent in the absence of acid.

3. A dihydrothiophene 1-oxide of the formula IIIa or IIIb:

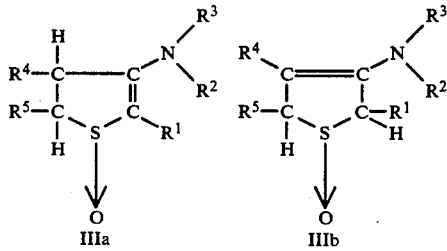

IIIa    IIIb in which $R^1$ to $R^5$, independently of one another, have the following meanings:

$R^1$, $R^4$ and $R^5$ are, independently of one another, hydrogen, $C_1$–$C_4$-alkyl radicals, $C_5$–$C_6$-cycloalkyl radicals, araliphatic radicals, aromatic radicals, alkoxycarbonyl, carboxamido, acyl radicals or CN; and $R^2$ and $R^3$ are, independently of one another, hydrogen; $C_1$–$C_4$-alkyl radicals, optionally substituted by $COOCH_3$, $COOC_2H_5$, OH, F, Cl, Br, ($C_1$–$C_4$)-alkoxy, $NH_2$ or ($C_1$–$C_8$)-alkylamino groups; $C_5$–$C_6$-cycloalkyl radicals, araliphatic radicals or aromatic radicals, optionally substituted by OH, $OCH_3$, $OC_2H_5$, F, Cl or Br; or acyl radicals; and, in addition, one of the two radicals $R^2$ and $R^3$ can also denote alkoxycarbonyl, or $R^2$ and $R^3$, together with the N atom to which they are attached, can also form a 5-membered to 7-membered ring which can also contain another heteroatom of the type O, S or N as a ring member.

4. The process for the preparation of a thiophene derivative of the formula I as claimed in the definition in claim 1, wherein an acid is added to a dihydrothiophene 1-oxide of the formula IIIa or IIIb:

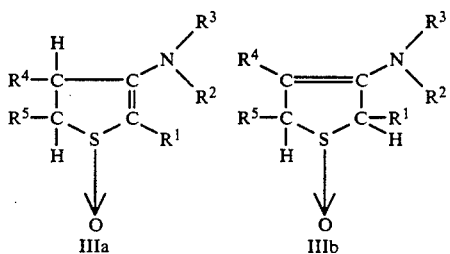

IIIa    IIIb in which $R^1$ to $R^5$ are as claimed in claim 1, in the course of which the dihydrothiophene 1-oxide undergoes rearrangement to give a thiophene derivative of the formula I.

5. The process as claimed in claim 1, wherein the radicals $R^1$ to $R^5$ in the formulae I, IIa and IIb have the following meaning:

$R^1$, $R^4$ and $R^5$ are, independently of one another hydrogen, $C_1$–$C_4$-alkyl, $C_5$–$C_6$-cycloalkyl, $CH_2$–$C_6H_5$, $C_6H_5$, $COOCH_3$, $COOC_2H_5$, $CONH_2$, $COCH_3$, $COC_2H_5$ or CN;

$R^2$ and $R^3$ are, independently of one another hydrogen, $C_1$–$C_4$-alkyl, optionally substituted by $COOCH_3$ or $COOC_2H_5$, $C_5$–$C_6$-cycloalkyl, $(CH_2)_{1-3}$–$C_6H_5$, $C_6H_5$, optionally substituted by OH, $OCH_3$, $OC_2H_5$, F, Cl or Br, or $CO(C_1$–$C_5$-alkyl) in which the alkyl radical can be substituted by OH, F, Cl, Br, ($C_1$–$C_4$)-alkoxy, $NH_2$ or ($C_1$–$C_8$)-alkylamino groups, and one of the radicals $R^2$ or $R^3$ can, in addition, also be $COOCH_3$ or $COOC_2H_5$, or $R^2$ and $R^3$, together with the N atom to which they are attached, form a pyrrolidino, piperidino, morpholino, piperazino or homopiperazino ring.

6. The process as claimed in claim 1, wherein the reaction is carried out in water or a neutral organic solvent, as a solvent or diluent.

7. The process as claimed in claim 2, wherein the radicals $R^1$ to $R^5$ in the formulae IIa, IIb, IIIa and IIIb have the following meaning:

$R^1$, $R^4$ and $R^5$ are, independently of one another, hydrogen, $C_1$–$C_4$-alkyl, $C_5$–$C_6$-cycloalkyl, $CH_2$—$C_6H_5$, $C_6H_5$, $COOCH_3$, $COOC_2H_5$, $CONH_2$, $COCH_3$, $COC_2H_5$ or CN;

$R^2$ and $R^3$ are, independently of one another, hydrogen, $C_1$-$C_4$-alkyl, optionally substituted by $COOCH_3$ or $COOC_2H_5$, $C_5$-$C_6$-cycloalkyl, $(CH_2)_{1-3}$—$C_6H_5$, optionally substituted by OH, $OCH_3$, $OC_2H_5$, Cl or Br, or $CO(C_1$-$C_5$-alkyl) in which the alkyl radical can be substituted by OH, F, Cl, Br, $(C_1$-$C_4)$-alkoxy, $NH_2$ or $(C_1$-$C_8)$-alkylamino groups, and one of the radicals $R^2$ or $R^3$ can, in addition, also be $COOCH_3$ or $COOC_2H_5$, or $R^2$ and $R^3$ together with the N atom to which they are attached, form a pyrrolidino, piperidino, morpholino, piperazino or homopiperazino ring.

8. The process as claimed in claim 2, wherein the reaction is carried out in water or a neutral organic solvent as a solvent or diluent.

9. The process as claimed in claim 4, wherein the radicals $R^1$ to $R^5$ in the formulae I, IIIa and IIIb have the following meaning:

$R^1$, $R^4$ and $R^5$ are, independently of one another, hydrogen, $C_1$-$C_4$-alkyl, $C_5$-$C_6$-cycloalkyl, $CH_2$—$C_6H_5$, $C_6H_5$, $COOCH_3$, $COOC_2H_5$, $CONH_2$, $COCH_3$, $COC_2H_5$ or CN;

$R^2$ and $R^3$ are, independently of one another, hydrogen, $C_1$-$C_4$-alkyl, optionally substituted by $COOCH_3$ or $COOC_2H_5$, $C_5$-$C_6$-cycloalkyl, $(CH_2)_{1-3}$—$C_6H_5$, optionally substituted by OH, $OCH_3$, $OC_2H_5$, Cl or Br, or $CO(C_1$-$C_5$-alkyl) in which the alkyl radical can be substituted by OH, F, Cl, Br, $(C_1$-$C_4)$-alkoxy, $NH_2$ or $(C_1$-$C_8)$-alkylamino groups, and one of the radicals $R^2$ or $R^3$ can, in addition, also be $COOCH_3$ or $COOC_2H_5$, or $R^2$ and $R^3$ together with the N atom to which they are attached, form a pyrrolidino, piperidino, morpholino, piperazino or homopiperazino ring.

10. The process as claimed in claim 4, wherein the reaction is carried out in water or a neutral organic solvent as a solvent or diluent.

11. A dihydrothiophene 1-oxide as claimed in claim 3, wherein the radicals $R^1$ to $R^5$ have the following meaning:

$R^1$, $R^4$ and $R^5$ are, independently of one another, hydrogen, $C_1$-$C_4$-alkyl, $C_5$-$C_6$-cycloalkyl, $CH_2$—$C_6H_5$, $C_6H_5$, $COOCH_3$, $COOC_2H_5$, $CONH_2$, $COCH_3$, $COC_2H_5$ or CN;

$R^2$ and $R^3$ are, independently of one another, hydrogen, $C_1$-$C_4$-alkyl, optionally substituted by $COOCH_3$ or $COOC_2H_5$, $C_5$-$C_6$-cycloalkyl, $(CH_2)_{1-3}$—$C_6H_5$, optionally substituted by OH, $OCH_3$, $OC_2H_5$, Cl or Br, or $CO(C_1$-$C_5$-alkyl) in which the alkyl radical can be substituted by OH, F, Cl, Br, $(C_1$-$C_4)$-alkoxy, $NH_2$ or $(C_1$-$C_8)$-alkylamino groups, and one of the radicals $R^2$ or $R^3$ can, in addition, also be $COOCH_3$ or $COOC_2H_5$, or $R^2$ and $R^3$, together with the N atom to which they are attached, form a pyrrolidino, piperidino, morpholino, piperazino or homopiperazino ring.

12. The process as claimed in claim 1, wherein the reaction is carried out in water, a $C_1$-$C_4$-alkanol or a mixture thereof.

13. The process as claimed in claim 2, wherein the reaction is carried out in water, a $C_1$-$C_4$-alkanol or a mixture thereof.

14. The process as claimed in claim 4, wherein the reaction is carried out in water, a $C_1$-$C_4$-ethanol or a mixture thereof.

* * * * *

UNITED STATES PATENT AND TRADEMARK OFFICE
CERTIFICATE OF CORRECTION

PATENT NO. : 5,166,346
DATED : November 24, 1992
INVENTOR(S) : Robert Rippel et al.

It is certified that error appears in the above-indentified patent and that said Letters Patent is hereby corrected as shown below:

Claim 7, column 13, line 7, after "$OC_2H_5$," insert --F,--.

Claim 9, column 13, line 29, after "$OC_2H_5$," insert --F,--.

Claim 11, column 14, line 17, after "$OC_2H_5$," insert --F,--.

Signed and Sealed this

Twenty-second Day of March, 1994

Attest:

BRUCE LEHMAN

*Attesting Officer*  *Commissioner of Patents and Trademarks*